(12) United States Patent
Yeh (10) Patent No.: US 10,821,014 B2
(45) Date of Patent: Nov. 3, 2020

(54) SUPPORT BRACE

(71) Applicant: Shih-Yuan Yeh, Taichung (TW)

(72) Inventor: Shih-Yuan Yeh, Taichung (TW)

( * ) Notice: Subject to any disclaimer, the term of this patent is extended or adjusted under 35 U.S.C. 154(b) by 329 days.

(21) Appl. No.: 16/022,313

(22) Filed: Jun. 28, 2018

(65) Prior Publication Data

US 2019/0142619 A1     May 16, 2019

(30) Foreign Application Priority Data

Nov. 10, 2017   (TW) ............................. 106216757 U (51) Int. Cl.
*A61F 5/01*     (2006.01)

(52) U.S. Cl.
CPC .......... *A61F 5/0102* (2013.01); *A61F 5/0195* (2013.01); *A61F 2005/0155* (2013.01); *A61F 2005/0167* (2013.01); *A61F 2005/0179* (2013.01)

(58) Field of Classification Search
CPC ...... A61F 2005/0167; A61F 2005/0158; A61F 2005/016; A61F 2005/0169; A61F 2005/0179; A61F 2005/0146; A61F 2005/0155; A61F 2005/0197; A61F 5/0195; A61F 5/0127; A61F 5/0111; A61F 5/0116; A61F 5/0193; A61F 5/04; A61F 5/042; A61F 5/048; A61F 5/0102; A61F 5/0104; A61F 5/0106; A61F 5/0123; A61F 5/024; A61F 5/026; E05F 3/02; E05F 3/22; E05F 3/108; E05D 11/10; E05D 11/1007; E05D 11/1014; E05D 11/1021; E05D 11/105; E05D 11/1028; E05D 11/1064

USPC ......... 16/319, 321, 323, 324, 326, 327, 333, 16/349, 71, 80, 70, 49, 66; 248/118.3, 248/59, 70, 122.1
See application file for complete search history.

(56) References Cited

U.S. PATENT DOCUMENTS

| | | | | |
|---|---|---|---|---|
| 3,588,023 | A * | 6/1971 | Cohen | F16B 2/246 248/410 |
| 5,224,681 | A * | 7/1993 | Lundstrom | F16B 2/246 24/522 |
| 5,501,543 | A * | 3/1996 | Schluter-Wohlfeil | B65H 75/08 403/321 |
| 9,375,342 | B2 * | 6/2016 | DeHeer | A61F 5/0127 |
| 2007/0234509 | A1 * | 10/2007 | Etlicher | E05F 1/105 16/66 |

* cited by examiner

*Primary Examiner* — Alireza Nia
*Assistant Examiner* — Kevin S Albers
(74) *Attorney, Agent, or Firm* — Sinorica, LLC (57) ABSTRACT

A support brace has a conjoining component, an extending component, a guiding set, an adjusting set, and an operating set. The guiding set has a guiding pole mounted to the conjoining component. The adjusting set is mounted to the extending component and has an adjusting sheet with a through hole located around and engaged with the guiding pole. The operating set has a pressing pole able to press the adjusting sheet and to disengage the through hole of the adjusting sheet and the guiding pole, and make the extending component to which the adjusting set is mounted moveable relative to the conjoining component along a moving direction. The support brace is longitudinally adjustable, is suitable for different limb lengths, and is able to reduce cost of casting orthopedic cast and purchasing appliances of orthotics of different sizes.

6 Claims, 8 Drawing Sheets

SUPPORT BRACE

BACKGROUND OF THE INVENTION

1. Field of the Invention

The present invention relates to a support brace, and more particularly to a support brace that is length-adjustable.

2. Description of Related Art

In order to facilitate a fracture to recover as soon as possible, when taking care of a patient suffering from a limb fracture, the medical staff fixes the fracture by orthopedic cast or other appliances of orthotics. The orthopedic cast and the appliances of orthotics cover the fracture and provide the fracture with both protection and supporting forces, thereby keeping the fracture from being moved unintentionally and prevent the fracture from damage again. The fracture can gradually recover in a still state.

However, limb length varies from one person to another, but the orthopedic cast and conventional appliances of orthotics are fixed in length and cannot fit the varying limb lengths of different persons. The orthopedic casts of different sizes require different molds for casting, and the conventional appliances of the orthotics of various sizes have to be purchased. Therefore, casting of the orthopedic cast and purchasing of the conventional appliances of orthotics that are not length-adjustable cost a lot.

To overcome the shortcomings of the orthopedic cast and the conventional appliances of orthotics, the present invention provides a support brace to mitigate or obviate the aforementioned problems.

SUMMARY OF THE INVENTION

The main objective of the present invention is to provide a support brace that is longitudinally adjustable for various limb lengths of different users.

The support brace comprises a conjoining component, an extending component, a guiding set, an adjusting set, and an operating set. The guiding set has a guiding pole mounted to the conjoining component. The adjusting set is mounted to the extending component and has an adjusting sheet with a through hole located around and engaged with the guiding pole. The operating set has a pressing pole able to press the adjusting sheet and to disengage the guiding pole from the through hole of the adjusting sheet, and make the extending component to which the adjusting set is mounted moveable relative to the conjoining component along a moving direction. The support brace is longitudinally adjustable, is suitable for different limb lengths of different people, and is able to reduce cost of casting orthopedic cast and purchasing appliances of orthotics of different sizes.

Other objects, advantages, and novel features of the invention will become more apparent from the following detailed description when taken in conjunction with the accompanying drawings.

DETAILED DESCRIPTION OF PREFERRED EMBODIMENTS

Figure 1:
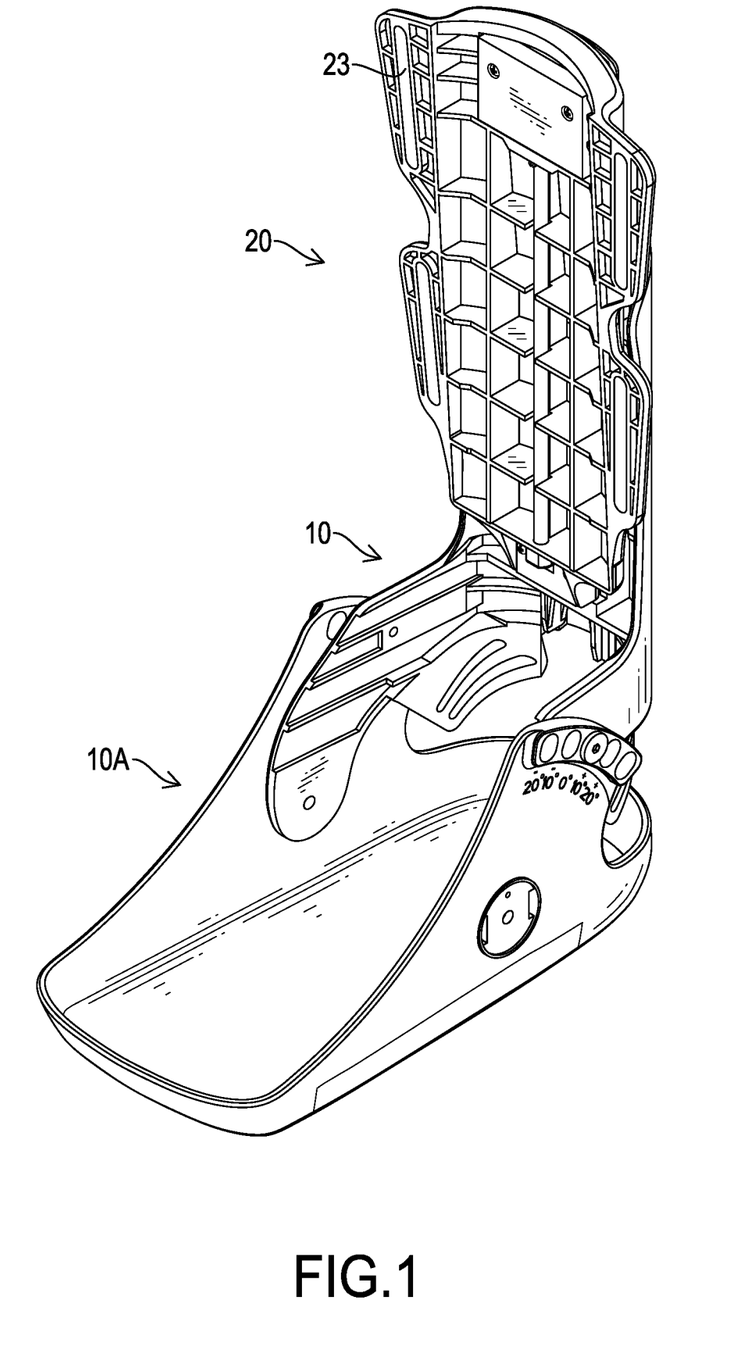
FIG. 1 is a perspective view of a support brace in accordance with the present invention.
Figure 2:
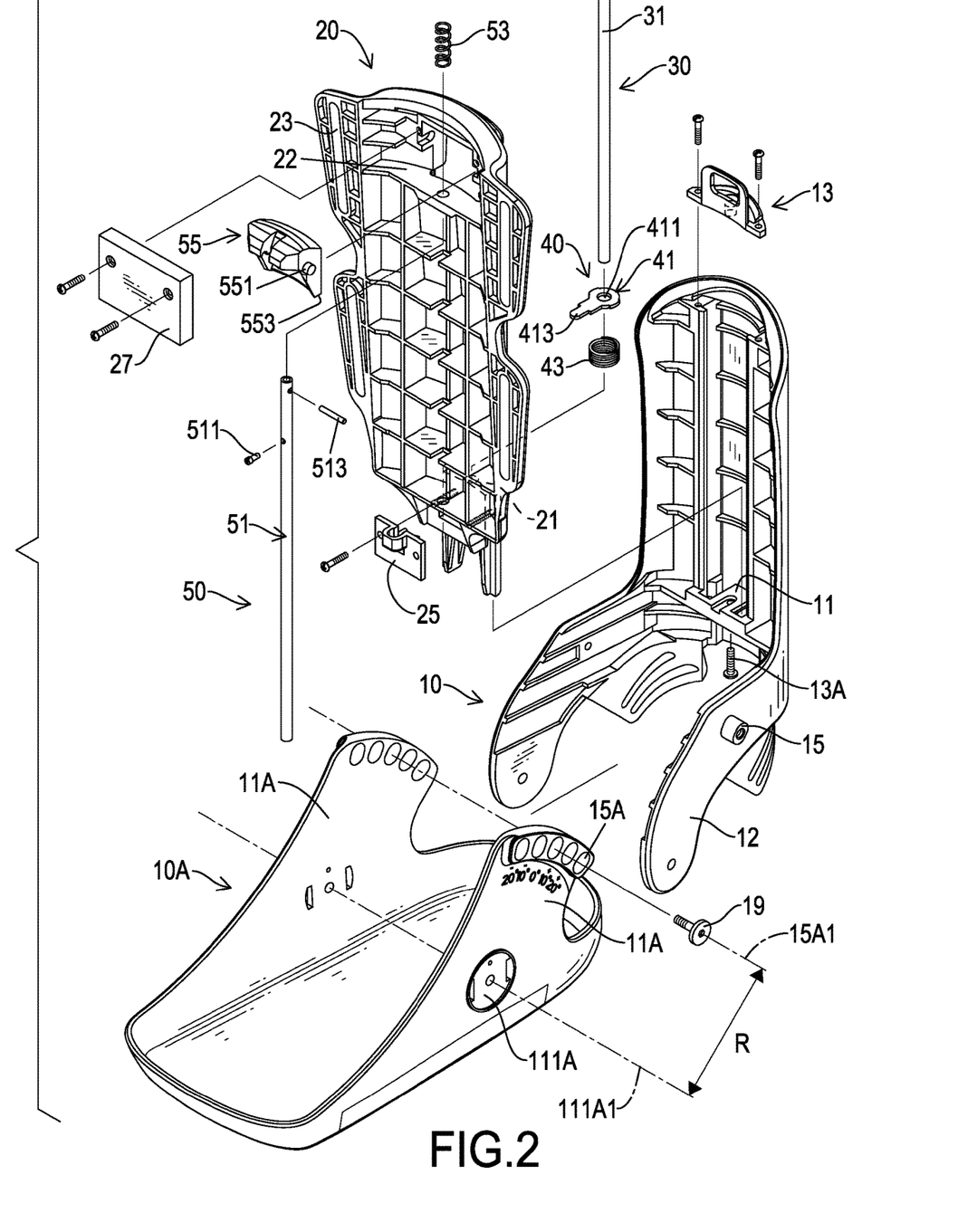
FIG. 2 is an exploded perspective view of the support brace in FIG. 1.

With reference to FIGS. 1 and 2, a support brace in accordance with the present invention has a conjoining component 10, an extending component 20, a guiding set 30, an adjusting set 40, an operating set 50, and a base 10A.

Figure 3:
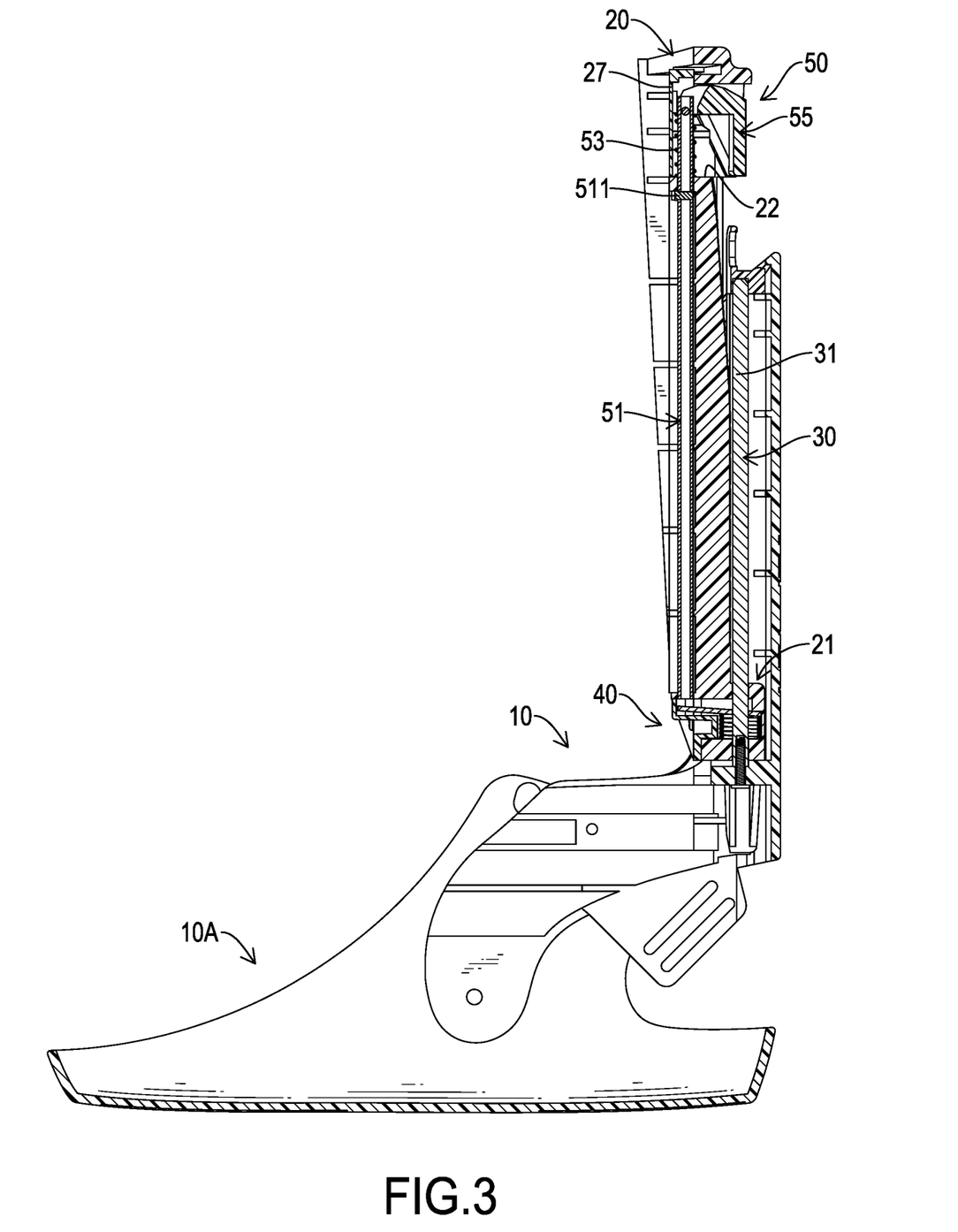
FIG. 3 is a cross-sectional side view of the support brace in FIG. 1.
Figures 4, 4A:
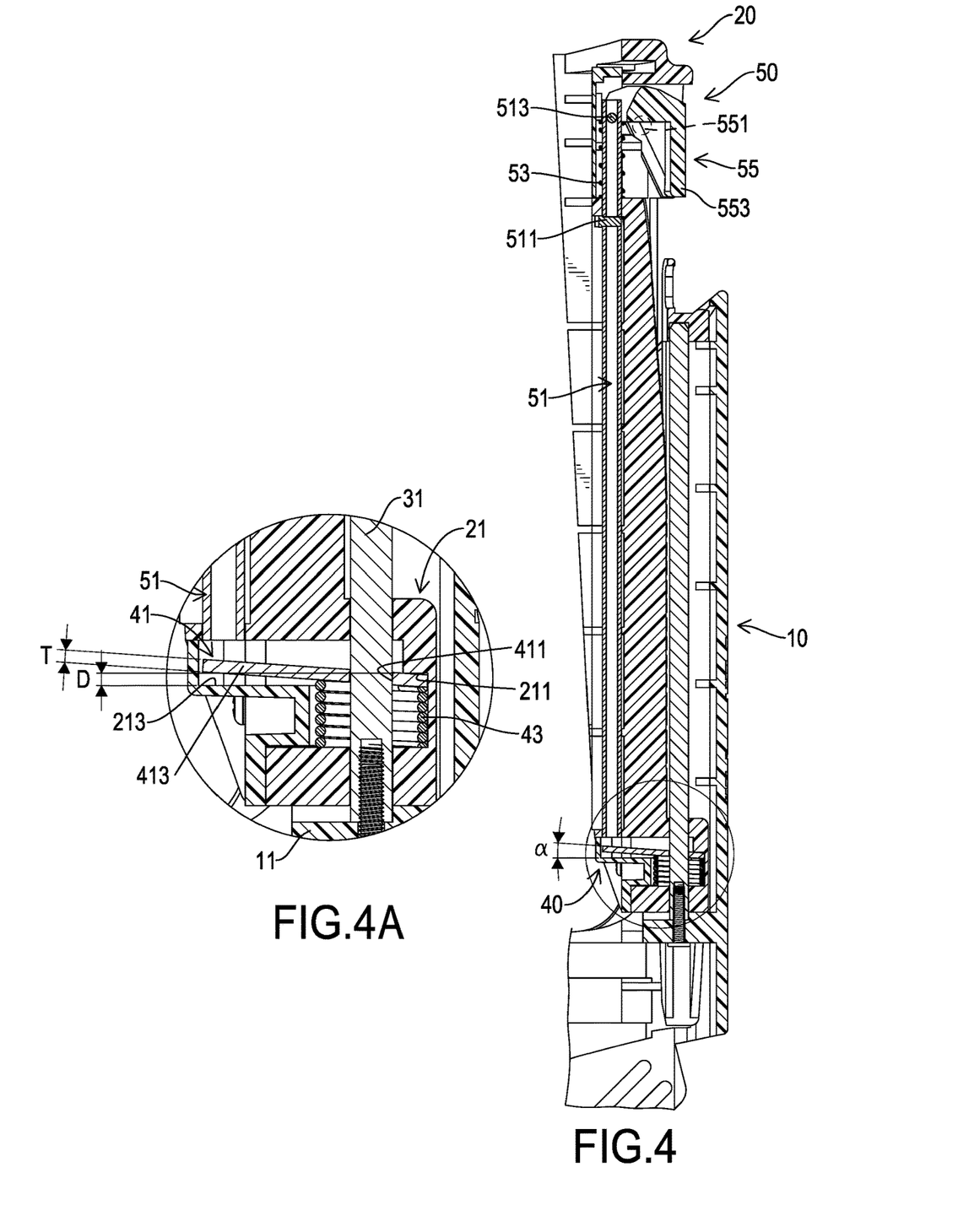
FIG. 4 is an enlarged cross-sectional side view of the support brace in FIG. 3.
FIG. 4A is a partially enlarged cross-sectional side view of the support brace in FIG. 4.

With reference to FIGS. 2 to 4, the conjoining component 10 has an erect portion, a first connecting portion 11, two pivoting arms 12, a holding unit 13, a fastening bolt 13A, and two engaging protrusions 15. The erect portion of the conjoining component 10 has an upper end, a lower end, a front side, and a rear side. The upper end and the lower end of the erect portion of the conjoining component 10 are opposite each other. The front side and the rear side of the erect portion of the conjoining component 10 face to opposite directions. The front side of the erect portion of the conjoining component 10 has multiple reinforcing ribs.

The first connecting portion 11 is formed at the front side of the erect portion of the conjoining component 10 and is disposed adjacent to the lower end of the erect portion of the conjoining component 10. The first connecting portion 11 is a platform for assembling the guiding set 30.

The two pivoting arms 12 are formed at the front side of the erect portion, are disposed below the first connecting portion 11, and extend away from the erect portion of the conjoining component 10. Each one of the two pivoting arms 12 has a pivoting portion disposed distal from the first connecting portion 11.

The holding unit 13 is assembled to the upper end of the erect portion of the conjoining component 10 by two bolts. The fastening bolt 13A is mounted through the first connecting portion 11 upward.

The two engaging protrusions 15 are coaxially and respectively formed at the two pivoting arms 12 and extend to opposite directions.

With reference to FIGS. 2 to 4, the extending component 20 is disposed in front of the conjoining component 10 and is moveable relative to the conjoining component 10 along a moving direction. The extending component 20 has a main portion, a second connecting portion 21, an assembling platform 22, two pairs of fixing holes 23, and a cover 27. The main portion of the extending component 20 is erectly disposed and has a top end, a bottom end, a front side, and a rear side. The top end and the bottom end of the main portion are opposite each other. The front side and the rear side of the main portion face to opposite directions. The front side of the main portion has multiple reinforcing ribs.

The second connecting portion 21 is formed at the bottom end of the main portion and has a rear limiting part, a first limiting face 211, a front limiting part 25, and a second limiting face 213. The rear limiting part is formed at the rear side of the main portion. The first limiting face 211 is disposed at the rear limiting part and faces downward. The front limiting part 25 is assembled to the rear limiting part by two bolts from the front side of the main portion. The second limiting face 213 is disposed at the front limiting part 25 and faces upward. The second limiting face 213 and the first limiting face 211 are separated by a distance D in the moving direction. The assembling platform 22 is formed at the front side of the main portion and is disposed adjacent to the top end of the main portion. The assembling platform 22 has an upward face and a downward face. The upward face and the downward face respectively face to the top end and the bottom end of the main portion. Each fixing hole 23 of one pair of the two pairs of fixing holes 23 is an elongated hole and is formed through the main portion. The cover 27 is mounted to the main portion by two bolts and covers the assembling platform 22.

With reference to FIGS. 2 to 4, the guiding set 30 is disposed between the erect portion of the conjoining component 10 and the main portion of the extending component 20. The guiding set 30 has a guiding pole 31. The guiding pole 31 has a cross-section in the moving direction. The cross-section of the guiding pole 31 has an area. The guiding pole 31 is mounted through the holding unit 13 downward, is mounted through the rear limiting part of the second connecting portion 21 of the extending component 20, and is screwed with the fastening bolt 13A to fix to the first connecting portion 11.

With reference to FIGS. 2 to 4, the adjusting unit 40 has an adjusting sheet 41 and a first elastic unit 43. The adjusting sheet 41 is a metal sheet and is disposed between the first limiting face 211 of the rear limiting part and the second limiting face 213 of the front limiting part 25.

The adjusting sheet 41 has a thickness T, a first end, a second end, a through hole 411, and a pressed portion 413. The thickness T is substantially equal to the distance D defined between the first limiting face 211 and the second limiting face 213. The first end and the second end of the adjusting sheet 41 are opposite each other. The first end of the adjusting sheet 41 faces to the rear limiting part of the second connecting portion 21. The second end of the adjusting sheet 41 faces to the front limiting part 25. The through hole 411 is disposed adjacent to the first end of the adjusting sheet 41. The through hole 411 has an outline. The outline of the through hole 411 encloses an area. The through hole 411 is located around the guiding pole 31, and the area enclosed by the outline of the through hole 411 is larger than the area of the cross-section of the guiding pole 31. The pressed portion 413 is disposed at the second end of the adjusting sheet 41. The first elastic unit 43 is a compression spring.

The first elastic unit 43 is mounted around the guiding pole 31 and abuts against both the first end of the adjusting sheet 41 and the second connecting portion 21. The first elastic unit 43 abuts against the first end of the adjusting sheet 41 to make the adjusting sheet 41 obliquely disposed relative to the guiding pole 31 and to make the through hole 411 of the adjusting sheet 41 engaged with the guiding pole 31.

With reference to FIGS. 2 to 4, the operating set 50 has a pressing pole 51, a limiting pin 511, a pressed stick 513, a second elastic unit 53, and an operating unit 55. The pressing pole 51 extends along the moving direction and is mounted through the assembling platform 22 of the conjoining component 20 downward. The limiting pin 511 is radially mounted through the pressing pole 51 and is disposed below the assembling platform 22. The pressed stick 513 is radially mounted through the pressing pole 51 and is disposed above the assembling platform 22. The second elastic unit 53 is a compression spring, is mounted around the pressing pole 51, and abuts against both the upward face of the platform 22 and the pressed stick 513. The operating unit 55 has two pivoting protrusions 551 and a pulling portion 553. The two pivoting protrusions 551 are pivotally connected to the main portion of the extending component 20 and make the operating unit 55 able to swing relative to the main portion of the extending component 20. The operating unit 55 is restricted both by the cover 27 and the main portion of the extending component 20.

With reference to FIGS. 2 to 4, the base 10A has a bottom, two connecting arms 11A, and multiple pairs of positioning openings 15A. The two connecting arms 11A extend from the bottom of the base 10A and each connecting arm 11A has a respective pivoting portion 111A. The two pivoting portions 111A are coaxially aligned along a pivoting axis 111A1. The multiple pairs of positioning openings 15A are arranged around the pivoting axis 111A1. The two positioning openings 15A of each pair are coaxially aligned along a positioning axis 15A1 that is away from the pivoting axis 111A1 by a distance R.

The two pivoting arms 12 of the conjoining component 10 are respectively and pivotally connected to the two connecting arms 11A and respectively fixed to the two connecting arms 11A by two bolts 19. The pair of the positioning protrusions 15 is mounted in one of the multiple pairs of positioning openings 15A.

With reference to FIGS. 4 and 4A, the first elastic unit 43 abuts against the first end of the adjusting sheet 41 and tilts the adjusting sheet 41 to be oblique relative to the guiding pole 31. An angle α is defined between the second end of the adjusting sheet 41 and a radial direction of the guiding pole 31. The through hole 411 of the adjusting sheet 41 that is oblique relative to the guiding pole 31 engages with the guiding pole 31 to restrict the adjusting sheet 41 and to prevent the adjusting sheet 41 from moving relative to the guiding pole 31. Therefore, the extending component 20 in which the adjusting sheet 41 is mounted cannot move relative to the conjoining component 10. With reference to FIG. 4A, the pressing pole 51 is separated from the pressed portion 413 of the adjusting sheet 41.

Figures 5, 5A:
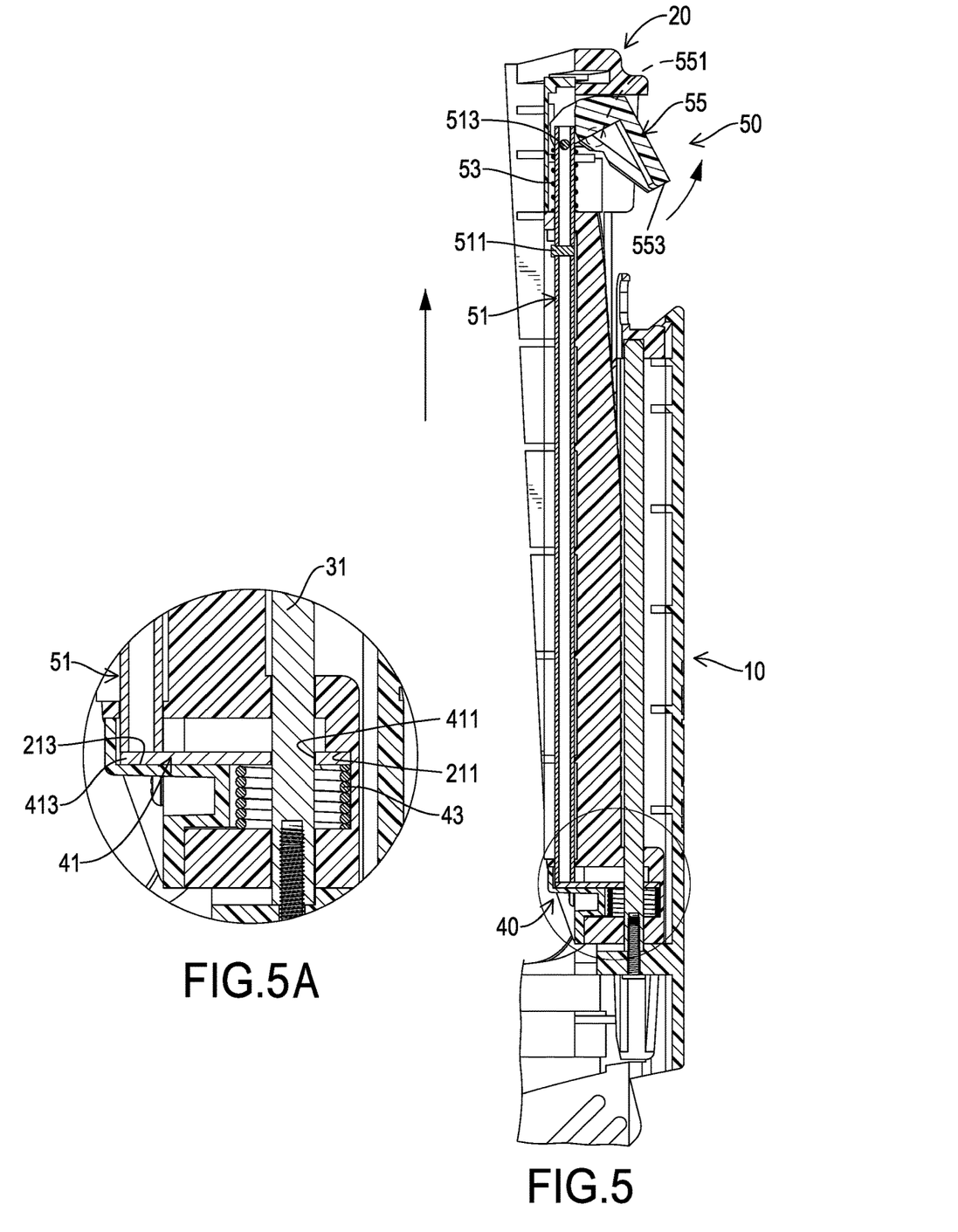
FIG. 5 is an enlarged schematic cross-sectional side view of the support brace in FIG. 4.
FIG. 5A is a partially enlarged schematic cross-sectional side view of the support brace in FIG. 5.

With reference to FIGS. 5 and 5A, when the pulling portion 553 of the operating unit 55 is pulled, the operating unit 55 rotates relative to the extending component 20 and presses the pressed stick 513 mounted to the pressing pole 51. The second elastic unit 53 is compressed by the pressed stick 513 and the assembling platform 22 of the extending component 20. The pressing pole 51 moves toward the pressed portion 413 of the adjusting sheet 41 and presses the pressed portion 413. Then, the adjusting sheet 41 swings counterclockwise in FIG. 4A, and the through hole 411 and the guiding pole 31 are disengaged from each other. Therefore, the extending component 20 is able to move relative to the conjoining component 10 along the guiding pole 31 for adjustment.

When the pulling portion 553 is released, the second elastic unit 53 restores and pushes the pressed stick 513 to lift the pressing pole 51, and the pressing pole 51 is detached from the pressed portion 413 of the adjusting sheet 41. The first elastic unit 43 pushes the first end of the adjusting sheet 41 again and makes the through hole 411 of the adjusting sheet 41 and the guiding pole 31 re-engage with each other.

Figure 6:
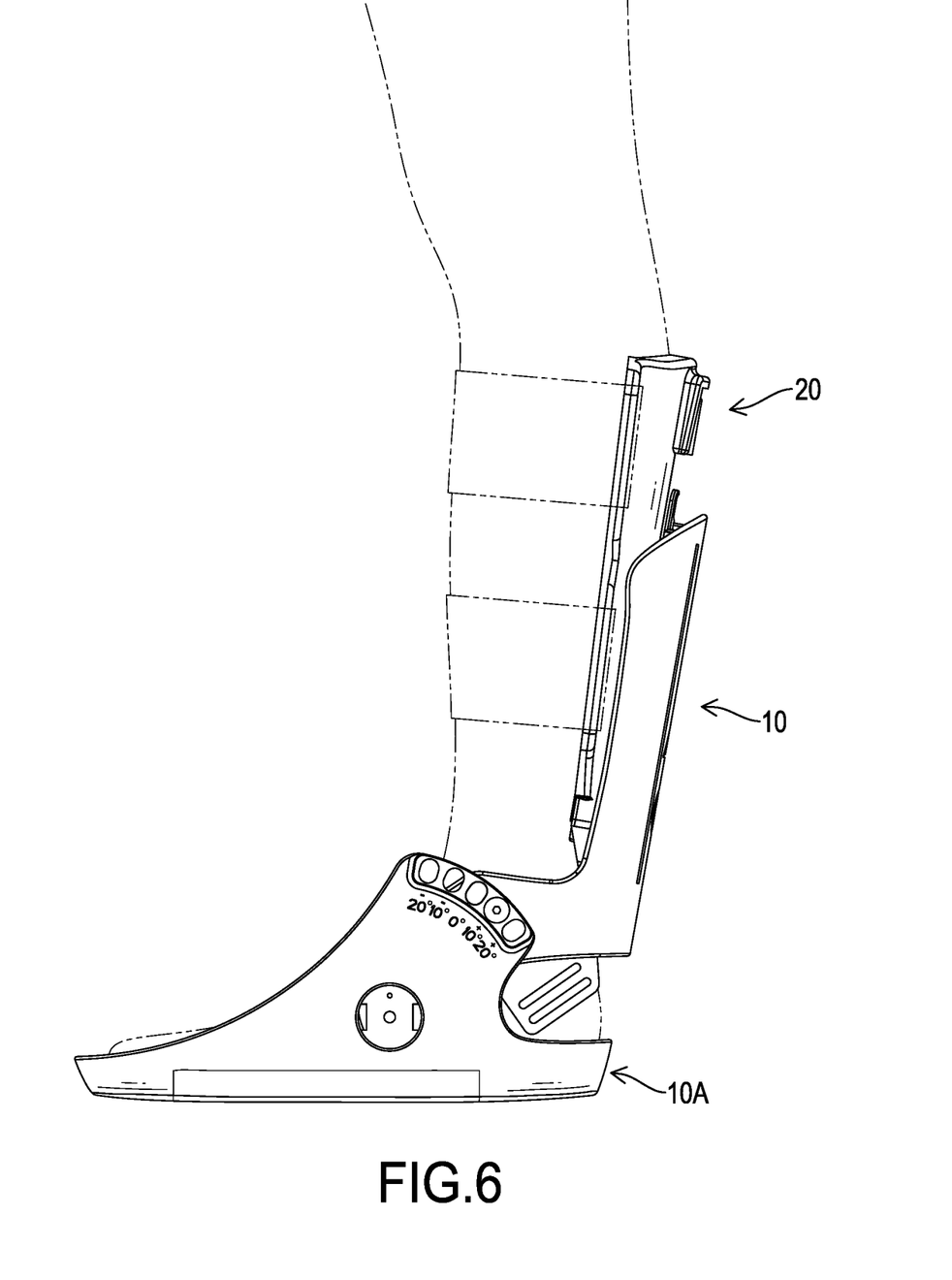
FIG. 6 is a schematic side view of the support brace in FIG. 1, showing the support brace is worn by a person.
Figure 7:
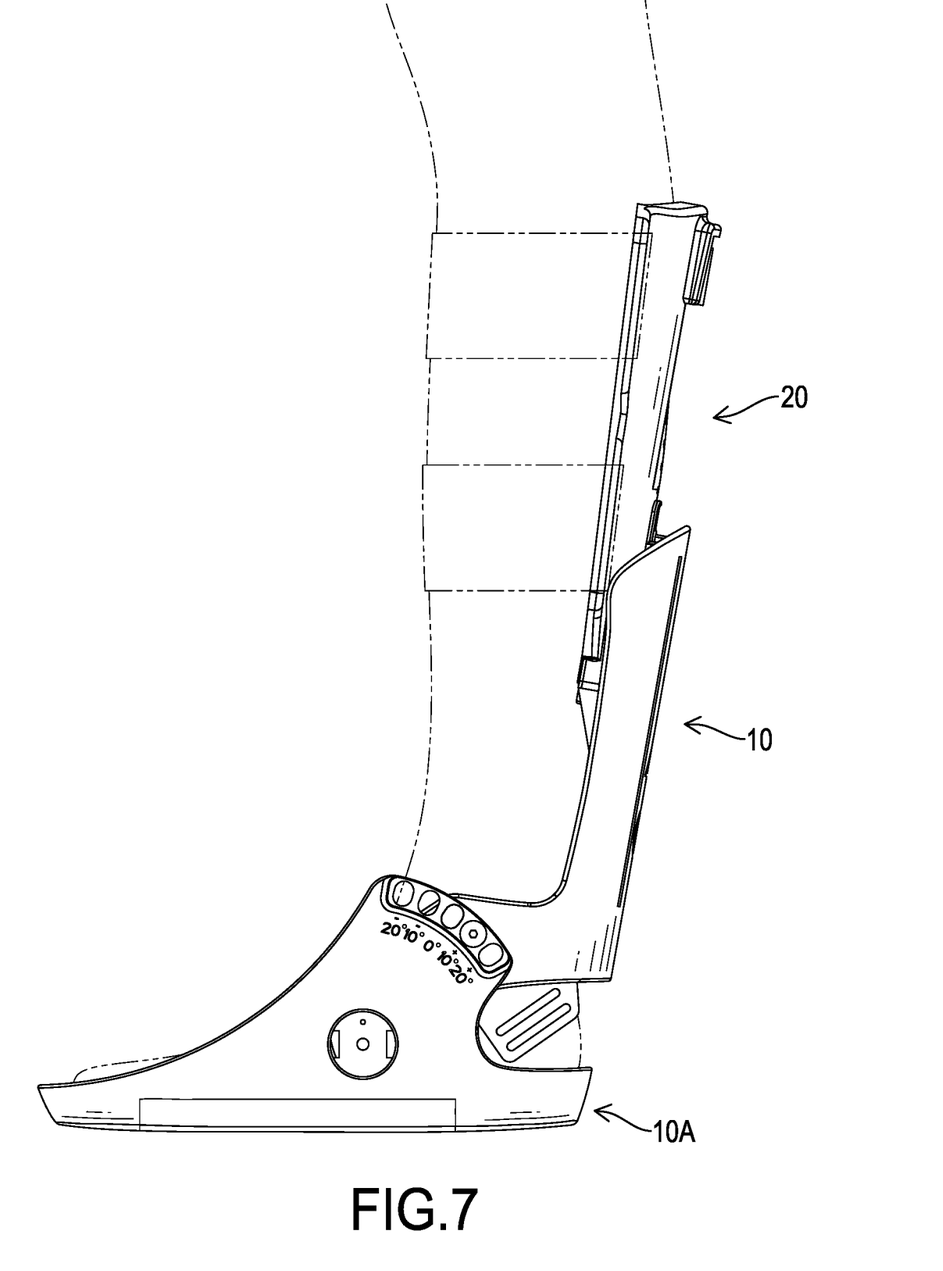
FIG. 7 is a schematic side view of the support brace in FIG. 1, showing an extending component moving relative to the conjoining component.

With reference to FIG. 6, two strips respectively pass through the two pairs of the fixing holes 23 and fix the support brace in accordance with the present invention to a calf of a wearer. With reference to FIGS. 6 and 7, the extending component 20 can be moved along the guiding pole 31 for longitudinal adjustment. The support brace in accordance with the present invention is adjustable, is suitable for different limb lengths, and is convenient to wear.

The guiding pole 31 may be fixed to the extending component 20, and the adjusting set 40 and the operating set 50 may be mounted to the conjoining component 10.

Figure 8:
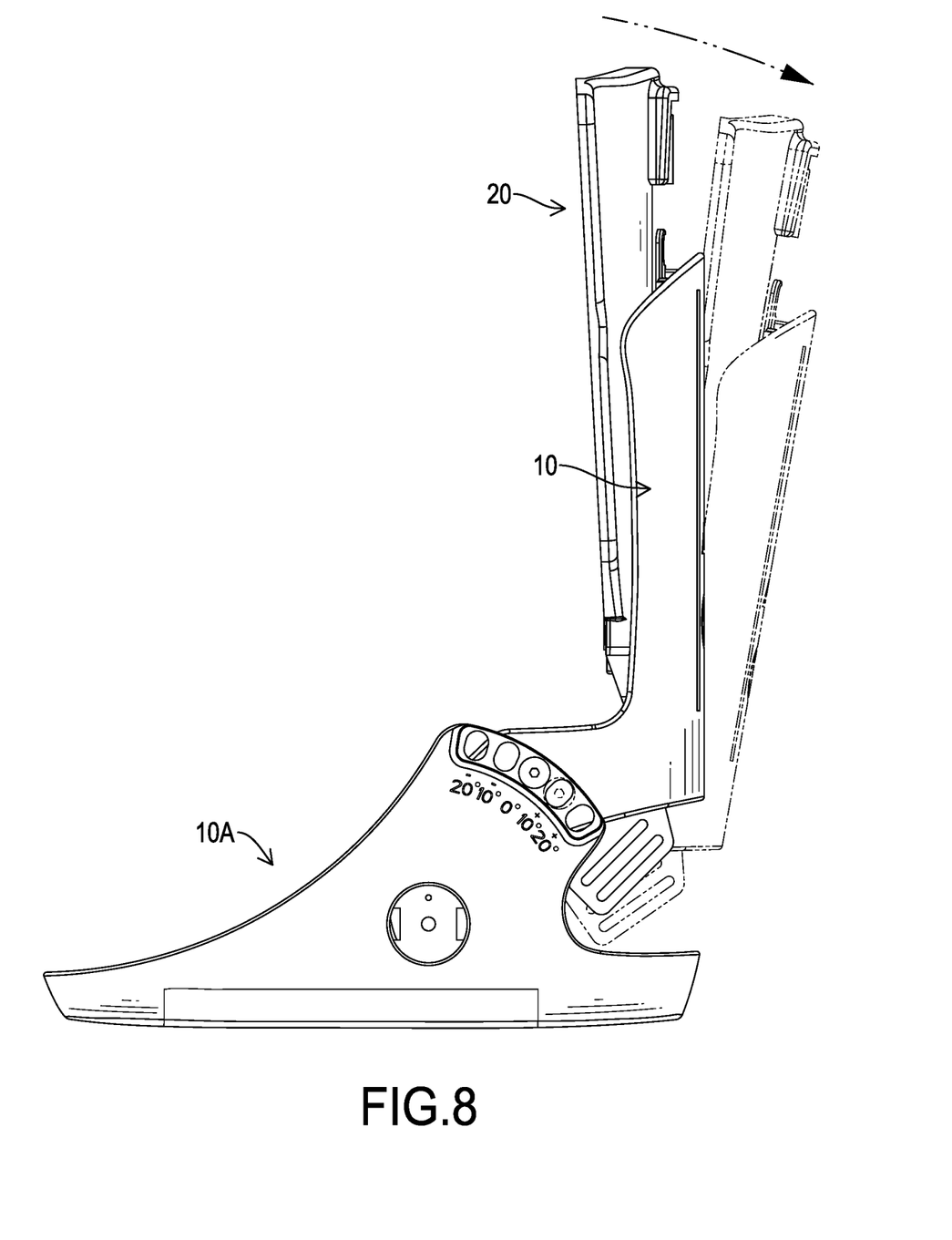
FIG. 8 is a schematic side view of the support brace in FIG. 1, showing the extending component and the conjoining component swinging relative to the base.

With reference to FIGS. 6 and 8, the conjoining component 10 is pivotally connected to the base 10A and is capable of swinging relative to the base 10A for adjusting obliqueness of the conjoining component 10 and the extending component 20. The two engaging protrusions 15 of the conjoining component 10 are respectively mounted in the two positioning holes 15A of one of the multiple pairs of the positioning holes 15A, preventing the conjoining component 10 and the extending component 20 from swinging relative to the base 10A unintentionally.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A support brace comprising:
    a conjoining component having a first connecting portion;
    an extending component having a second connecting portion connected to the first connecting portion, capable of moving relative to the first connecting portion along a moving direction, and having a first limiting face and a second limiting face;
    the first limiting face of the second connecting portion and the second limiting face of the second connecting portion facing to opposite directions and separated by a distance in the moving direction;
    a guiding set disposed between the conjoining component and the extending component and having
        a guiding pole being a metal pole, extending along the moving direction, fixed to the first connecting portion, and having a cross-section with an area in the moving direction;
    an adjusting set having
        an adjusting sheet, disposed between the first limiting face and the second limiting face, being a metal sheet, and having
            a thickness being equal to the distance defined between the first limiting face and the second limiting face;
            a first end;
            a second end opposite to the first end of the adjusting sheet;
            a through hole disposed adjacent to the first end of the adjusting sheet, having an outline enclosing an area larger than the area of the cross-section of the guiding pole, and located around the guiding pole; and
            a pressed portion disposed at the second end of the adjusting sheet; and
        a first elastic unit abutting against the first end of the adjusting sheet, tilting the adjusting sheet to be obliquely disposed relative to the guiding pole, and making the through hole of the adjusting sheet engaged with the guiding pole; and
    an operating set having
        a pressing pole extending along the moving direction, being moveable relative to the adjusting sheet, and being capable of pressing the pressed portion of the adjusting sheet;
        a pressing stick radially mounted to the pressing pole; and
        a second elastic unit abutting against the pressing pole and being capable of pushing the pressing pole away from the adjusting sheet.

2. The support brace as claimed in claim 1, wherein
    the operating set has an operating unit;
    the operating unit has
        two pivoting protrusions disposed coaxially; and
        a pulling portion for manual operation;
    the operating unit is pivotally connected to the extending component by the two pivoting protrusions and able to press the pressing stick mounted to the pressing pole when the pulling portion is pulled.

3. The support brace as claimed in claim 2, wherein
    the supporting brace has a base pivotally connected to the conjoining component and able to swing relative to the conjoining component with respect to a pivoting axis;
    the base has multiple pairs of positioning openings arranged around the pivoting axis;
    the two positioning openings of each pair are coaxially aligned along a positioning axis, parallel to the pivoting axis, and separated from the pivoting axis by a distance; and
    the conjoining component has two engaging protrusions respectively mounted in the two positioning openings of one of the multiple pairs of the positioning openings.

4. The support brace as claimed in claim 3, wherein
    the conjoining component has two pairs of fixing holes;
    each fixing hole of one of the two pairs of fixing holes is an elongated hole; and
    each pair of the fixing holes is mounted through by a strip.

5. The support brace as claimed in claim 1, wherein
    the supporting brace has a base pivotally connected to the conjoining component and able to swing relative to the conjoining component with respect to a pivoting axis;
    the base has multiple pairs of positioning openings arranged around the pivoting axis;
    the two positioning openings of each pair are coaxially aligned along a positioning axis, parallel to the pivoting axis, and separated from the pivoting axis by a distance; and
    the conjoining component has two engaging protrusions respectively mounted in the two positioning openings of one of the multiple pairs of the positioning openings.

6. The support brace as claimed in claim 1, wherein
    the conjoining component has two pairs of fixing holes;
    each fixing hole of one of the two pairs of fixing holes is an elongated hole; and
    each pair of the fixing holes is mounted through by a strip.

* * * * *